United States Patent [19]

Hirsch et al.

[11] Patent Number: 5,542,916
[45] Date of Patent: Aug. 6, 1996

[54] DUAL-CHANNEL RF POWER DELIVERY SYSTEM

[75] Inventors: Chaya Hirsch, Palo Alto, Calif.;
Robert Hale, Plymouth, England;
Bruno Strul, Palo Alto, Calif.

[73] Assignee: Vidamed, Inc., Menlo Park, Calif.

[21] Appl. No.: 314,190

[22] Filed: Sep. 28, 1994

Related U.S. Application Data

[63] Continuation-in-part of Ser. No. 929,638, Aug. 12, 1992, abandoned, and a continuation-in-part of Ser. No. 12,370, Feb. 2, 1993, Pat. No. 5,370,675, and a continuation-in-part of Ser. No. 61,072, May 14, 1993, Pat. No. 5,385,544, and a continuation-in-part of Ser. No. 216,315, Mar. 23, 1994, Pat. No. 5,484,400.

[51] Int. Cl.⁶ ............................................... A61B 17/20
[52] U.S. Cl. .................. 604/22; 604/164; 606/48; 607/74; 607/101
[58] Field of Search .................. 604/22, 164, 280; 606/41, 45, 50, 48; 607/99, 101, 109, 74

[56] References Cited

U.S. PATENT DOCUMENTS

| | | |
|---|---|---|
| 3,941,121 | 3/1976 | Olinger et al. . |
| 4,311,154 | 1/1982 | Sterzer et al. . |
| 4,312,364 | 1/1982 | Convert et al. . |
| 4,336,809 | 6/1982 | Clark . |
| 4,397,314 | 8/1983 | Vaguine . |
| 4,448,198 | 1/1984 | Turner . |
| 4,669,475 | 6/1987 | Turner . |
| 4,676,258 | 6/1987 | Inokuchi et al. . |
| 4,785,829 | 11/1988 | Convert et al. . |
| 4,907,589 | 3/1990 | Cosman . |
| 4,994,062 | 2/1991 | Nishigaki et al. . |
| 5,122,137 | 6/1992 | Lennox . |
| 5,197,466 | 3/1993 | Marchosky et al. . |
| 5,220,927 | 6/1993 | Astrahan et al. . |
| 5,249,585 | 10/1993 | Turner et al. . |
| 5,269,780 | 12/1993 | Roos ........................................ 606/42 |
| 5,273,524 | 12/1993 | Fox et al. . |
| 5,312,392 | 5/1994 | Hofstetter et al. . |
| 5,334,193 | 8/1994 | Nardella ..................................... 606/41 |
| 5,417,687 | 5/1995 | Nardella et al. ........................... 606/32 |
| 5,419,767 | 9/1995 | Eggers et al. ............................. 604/114 |

FOREIGN PATENT DOCUMENTS

0219216A1 4/1987 European Pat. Off. .

*Primary Examiner*—Randall L. Green
*Assistant Examiner*—A. T. Nguyen
*Attorney, Agent, or Firm*—Flehr, Hohbach, Test, Albritton & Herbert

[57] ABSTRACT

A dual-channel RF power delivery system for applying RF energy to dual electrodes of an RF ablation device with independent control of the power level, frequency, phase, and time duration of the RF energy applied to each electrode to more accurately control the ablation of a target tissue. The power delivery system supplies a first controlled RF signal having a first power level, frequency, phase, and time duration to the electrode of a first flexible stylet and a second controlled RF signal having a second power level frequency, phase, and time duration to the electrode of a second flexible stylet. The difference between the first and second power levels and the temperature of the tissue between the first and second stylers are monitored to control the ablation of the target tissue. The supply of the first RF signal is terminated when the monitored temperature of the first stylet exceeds a first predetermined value and the supply of the second RF signal is terminated when the monitored temperature of the second stylet exceeds a second predetermined value. By adjusting the frequency and/or phase of the first and second RF signals, the relative amounts of bipolar and monopolar ablation can be adjusted for accurate control of the lesion volume. The lesion volume can also be controlled by varying the deployment length of the electrodes.

8 Claims, 6 Drawing Sheets

MONOPOLAR RF ABLATION

BIPOLAR RF ABLATION

COMBINED MONOPOLAR & BIPOLAR RF ABLATION

*FIG. 6*

DUAL-CHANNEL RF POWER DELIVERY SYSTEM

RELATIONSHIP TO COPENDING APPLICATION

This patent application is a continuation-in-part of patent application Ser. No. 07/929,638 filed on Aug. 12, 1992 now abandoned, patent application Ser. No. 08/012,370 filed on Feb. 2, 1993, now U.S. Pat. No. 5,370,675, patent application Ser. No. 08/061,072 filed on May 14, 1993, now U.S. Pat. No. 5,385,544 and patent application Ser. No. 08/216,315 filed on Mar. 23, 1994, now U.S. Pat. No. 5,484,400 the entire contents of which are hereby incorporated by reference.

BACKGROUND OF THE INVENTION

This invention relates generally to techniques for delivering radiofrequency (RF) energy for the ablation of cellular tissue and, more particularly, to techniques for delivering RF energy for the ablation of prostate tissue for the treatment of benign prosthetic hypertrophy or hyperplasia (BPH).

Benign prostatic hypertrophy or hyperplasia (BPH) is one of the most common medical problems experienced by men over 50 years old. Hyperplastic enlargement of the prostate gland often leads to compression of the urethra, resulting in obstruction of the urinary tract and the subsequent development of various symptoms, including frequent urination, a decrease in urinary flow, nocturia, pain, discomfort, and dribbling. The association of BPH with aging has been shown to exceed 50% in men over 50 years of age and increases in incidence to over 75% in men over 80 years of age. Symptoms of urinary tract obstruction occur most frequently between the ages of 65 and 70, when approximately 65% of men in this age group have prostatic enlargement.

At the present time, there is no proven effective nonsurgical method for the treatment of BPH and the current surgical procedures are not totally satisfactory. Patients suffering from the obstructive symptoms of this disease are provided with few options: cope with the symptoms (conservative management), submit to drug therapy at an early stage, or submit to one of the current surgical procedures. More than 30,000 patients per year undergo surgery in the United States for the removal of prostatic tissue. This represents less than five percent of the men exhibiting clinically significant symptoms.

Those suffering from BPH are often elderly men, many with additional health problems which increase the risks of surgical procedures. Surgical procedures for the removal of prostatic tissue are associated with a number of complications, including anesthesia associated morbidity, hemorrhage, coagulopathies, pulmonary emboli and electrolyte imbalances. These surgical procedures can also lead to cardiac complications, bladder perforation, incontinence, infection, urethral or bladder neck stricture, retention of prostatic chips, retrograde ejaculation, and infertility. Due to the extensive invasive nature of the current surgical procedures for obstructive uropathy, the majority of patients delay definitive treatment of BPH. This can lead to serious damage to structures secondary to the obstructive lesion in the prostate, such as bladder hypertrophy, hydronephrosis, and dilation of the kidney pelves. Furthermore, younger men suffering from BPH who wish to avoid risk complications, such as infertility, are often forced to avoid surgical intervention. Thus the need, importance and value of improved surgical and nonsurgical methods for treating BPH is unquestionable.

High-frequency currents are used in various electrocautery procedures for cutting human tissue, especially when a bloodless incision is desired or when the operating site is not accessible with a normal scalpel. In the latter instance, a thin instrument can be inserted through a natural body opening, such as the esophagus, intestine or urethra, for the removal of prostatic adenomas, bladder tumors or intestinal polyps. The high-frequency current is fed by a surgical probe into the tissue to be cut, causing boiling and vaporization of the cell fluid so that the cell walls rupture and the tissue is separated.

Ablation of cellular tissues in situ has been used in the treatment of many diseases and medical conditions either alone or as an adjunct to surgical removal procedures. It is often less traumatic than surgical procedures and may be the only alternative where other procedures are unsafe. Ablation devices have the advantage of using a destructive energy that is rapidly dissipated and reduced to a non-destructive level by conduction and convection forces of circulating fluids and other natural body processes.

Ablation devices typical utilize microwave, radiofrequency (RF), acoustical (ultrasound), or laser energy. Microwave ablation devices utilize a microwave antenna which is inserted into a natural body opening through a duct to the zone of treatment. Microwave energy is then radiated from the antenna through the duct wall into the target tissue, often causing severe trauma to the duct wall. Consequently, many microwave ablation devices use a cooling system to help reduce this trauma. However, the cooling system complicates the device and requires that the device be sufficiently large to accommodate the cooling system. Laser ablation devices deliver laser energy to the target tissue by "burning through" the duct wall of the urethra. Healthy cells of the duct wall and healthy tissue between the target tissue and the duct wall are also indiscriminately destroyed in the process.

SUMMARY OF THE INVENTION

It is an object of the present invention to provide a dual-channel radiofrequency (RF) power delivery system for applying RF energy to dual electrodes of an RF ablation device with independent control of the power level, frequency, phase and time duration of the RF energy applied to each electrode to more accurately control the ablation of a target tissue.

It is a further object of the present invention to provide an RF power delivery system that performs self-testing by loading each power generator with an internal test load.

It is a further object of the present invention to provide calibration of temperature-measuring amplifier circuitry by switching precision reference voltage sources into the amplifier circuitry.

The present invention resides in a dual-channel RF power delivery system for applying RF energy to dual electrodes of an RF ablation device with independent control of the power level, frequency, phase, and time duration of the RF energy applied to each electrode to more accurately control the ablation of the target tissue. The power delivery system supplies a first controlled RF signal having a first power level, frequency, phase, and time duration to the electrode of a first flexible stylet and a second controlled RF signal having a second power level, frequency, phase, and time duration to the electrode of a second flexible stylet. The difference between the first and second power levels and the temperature of the tissue between the first and second stylets are monitored to control the ablation of the target tissue. The supply of the first RF signal is terminated when the monitored temperature of the first stylet exceeds a first predetermined value and the supply of the second RF signal is terminated when the monitored temperature of the second stylet exceeds a second predetermined value. By adjusting the frequency and/or phase of the first and second RF signals, the relative amounts of bipolar and monopolar ablation can be adjusted for accurate control of the lesion volume. The lesion volume can also be controlled by varying the deployment length of the electrodes.

It will be appreciated from the foregoing that the present invention represents a significant advance in the field of RF ablation devices. Other features of the present invention will become apparent from the following more detailed description, taken in conjunction with the accompanying drawings, which illustrate, by way of example, the principles of the invention.

DETAILED DESCRIPTION OF THE PREFERRED EMBODIMENTS

Figure 1:
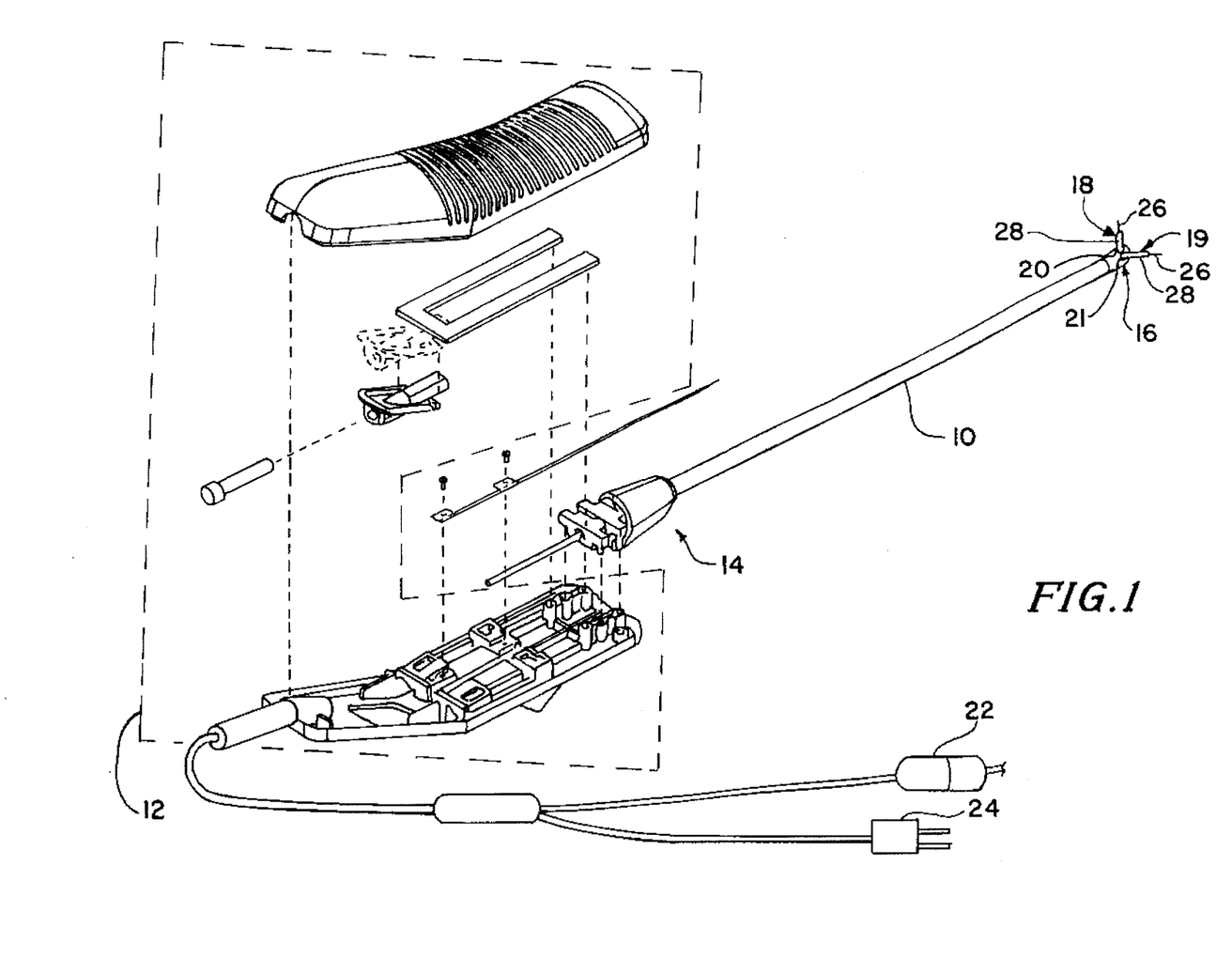
FIG. 1 is an exploded perspective view of a dualostylet RF ablation device which is suitable for use with the RF power delivery system of the present invention.

As shown in FIG. 1, a dual-stylet RF ablation device includes a flexible catheter 10 which is attached to a control unit 12 by means of a connector 14. The flexible catheter 10 includes a distal tip 16 having two stylets 18, 19, which extend outwardly from stylet ports 20, 21. The control unit 12 includes an RF power connector 22 and a thermocouple connector 24. The catheter 10 preferably has a graduated stiffness for easier insertion through a natural body opening into a body duct. For example, the catheter 10 can be relatively stiff near the control unit 12 and more flexible near the distal tip 16. The catheter 10 can be constructed of an inner slotted stainless steel tube with an outer flexible sleeve, such as the catheter described in detail in copending application Ser. No. 08/126,431 filed Sep. 24, 1993, now U.S. Pat. No. 5,322,064, the entire contents of which are incorporated herein by reference. It can also be constructed of a coiled or braided wire having a bonded outer sleeve.

Figure 2:
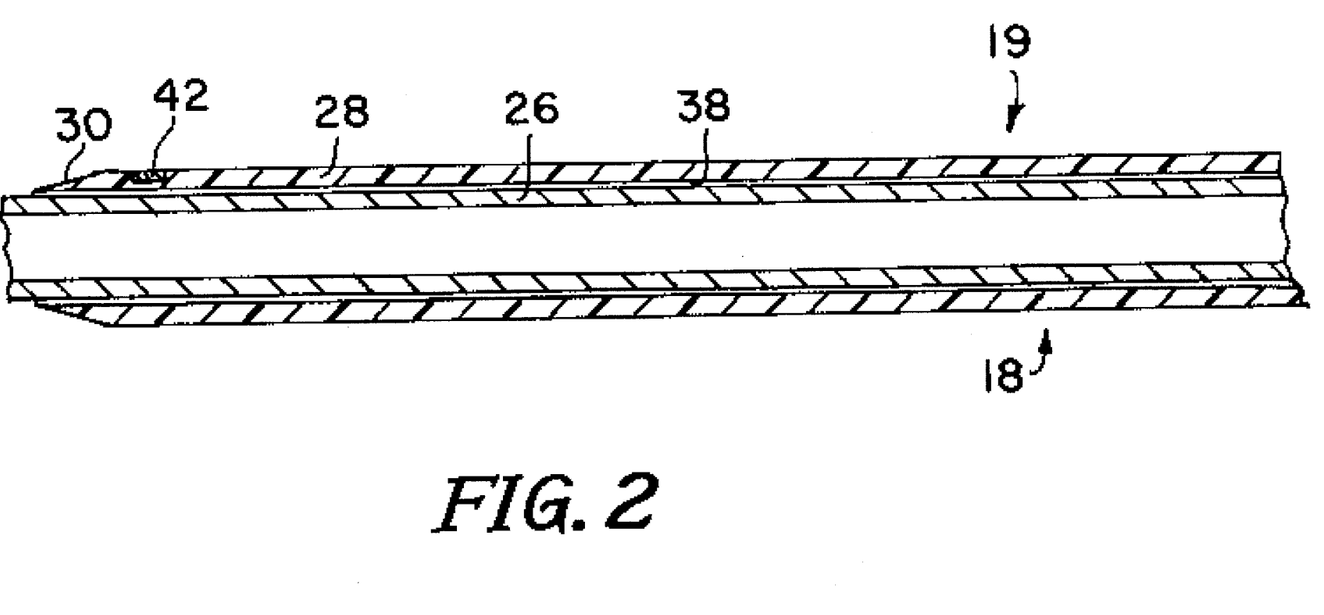
FIG. 2 is a cross-sectional view of a styler of the RF ablation device.

Each stylet 18, 19 includes an electrode 26 enclosed within a retractable insulating sleeve 28. The stylets 18, 19 are described in detail in the copending application Ser. No. 08/012,370 filed Feb. 2, 1993, now U.S. Pat. No. 5,370,675. As shown in FIG. 2, the insulating sleeve 28 has a tapered tip 30. The electrode 26 is slidably disposed in the center portion or lumen 38 of the insulating sleeve 28. A temperature sensor 42 is mounted near the tapered tip 30 of the insulating sleeve 28 for measuring the temperature of a target tissue as it is ablated.

Figure 3:
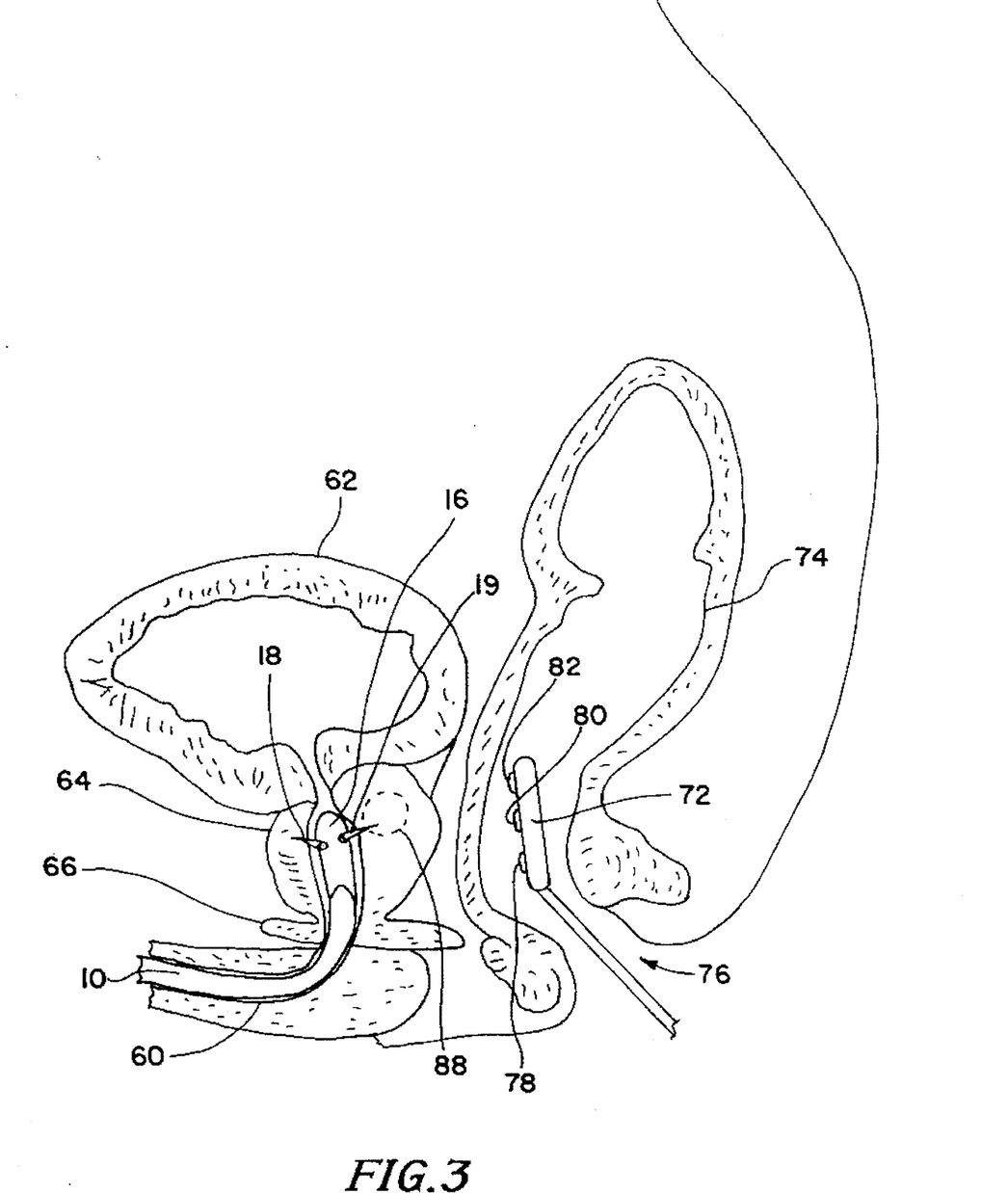
FIG. 3 is a cross-sectional view of the lower male anatomy.

FIG. 3 is a cross-sectional view of the lower male anatomy in which the catheter 10 of the RF ablation device is positioned near a prostate for treatment of benign prostatic hypertrophy or hyperplasia (BPH). As shown in FIG. 3, the human male has a urethra 60 which extends from urinary bladder 62 through prostate 64 and urogenital diaphragm 66. Benign prostatic hypertrophy (BPH) is a condition characterized by constriction of the prostatic urethra 60, which is caused primarily by proliferation of benign glandular and stroma cells in the prostate. The resulting glandular and stroma nodules press the wall of the urethra inwardly, restricting the urethral diameter. These nodules also press normal tissue outwardly, which enlarges the prostate. Traditional treatments have included removal of tissue from the urethra wall to enlarge its lumen, either by resection or laser tissue destruction, and heating of the prostate tissue surrounding the urethra to a temperature that causes cell damage. The latter method is intended to reduce the enlargement of the prostate and restore the urinary passage to at least a portion of its former diameter.

The catheter 10 is extended through the urethra 60 such that the distal tip 16 of the catheter 10 is adjacent the prostate 64. The position of the distal tip 16 may be precisely controlled using an ultrasound image, which is generated from a conventional ultrasonic transducer 72. Ultrasonic transducer 72 is preferably inserted into rectum 74 through anal opening 76 to a position adjacent the prostate. The transducer 72 may include temperature sensors 78, 80, 82 for measuring the temperature of the rectal area in order to alert the user to any adverse effects that may result from the heating of the prostate tissue. Sensors 78, 80, 82 may also be placed on a separate instrument that is positioned in the rectal area after the catheter 10 is properly positioned and the ultrasonic transducer 72 is removed. In FIG. 3, stylet 19 is extended into tissue area 88 which represents tissue to be ablated.

Figure 4:
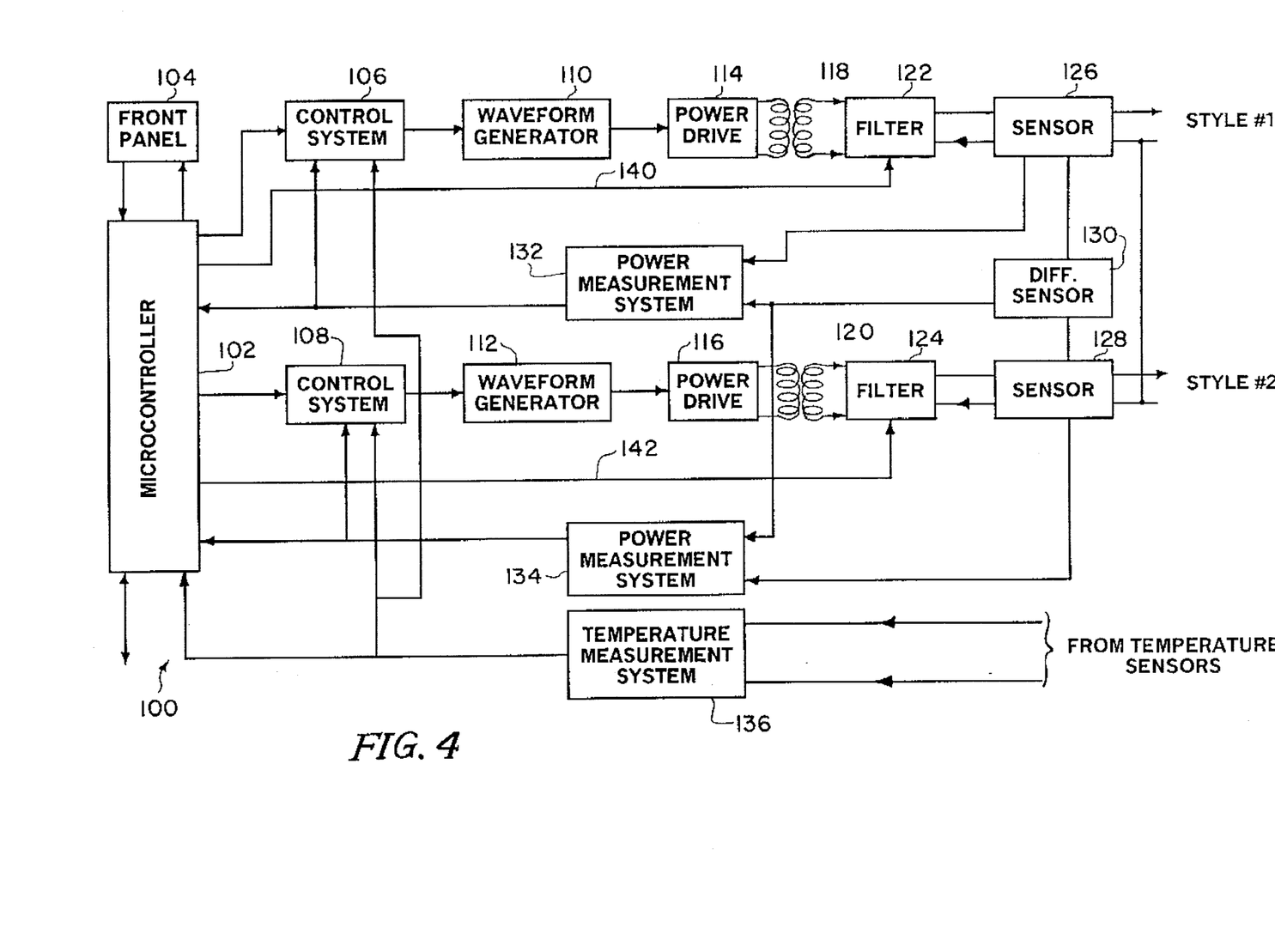
FIG. 4 is block diagram of the RF power delivery system of the present invention.

FIG. 4 is a block diagram of a dual-channel RF power delivery system 100 in accordance with the present invention. Power delivery system 100 generates dual RF signals which are applied to the target prostate tissue through the two stylets 18, 19. Power delivery system 100 includes a microcontroller 102, a front panel 104, parallel control systems 106, 108, parallel dual waveform generators 110, 112, parallel power drives 114, 116, parallel isolators 118, 120, parallel filters 122, 124, parallel sensors 126, 128, a differential sensor 130, power measurement systems 132, 134, a temperature measurement system 136, and a foot switch (not shown). The control system 106, waveform generator 110, power drive 114, isolator 118, filter 122, and sensor 126 are connected in series and form a first power delivery channel. The control system 108, waveform generator 112, power drive 116, isolator 120, filter 124, and sensor 128 are connected in series and form a second power delivery channel.

The microcontroller 102 receives user input information from the front panel 104. Digital feedback information is also received from the temperature measurement system 136 and the power measurement systems 132 and 134. The microcontroller 102 processes this information and generates command signals for controlling the outputs of the dual power delivery channels. The microcontroller 102 includes a conventional microprocessor, random access memory (RAM), and read only memory (ROM) (not shown). The software necessary for operation of the microprocessor is typically stored in the ROM.

The front panel 104 may include different displays for displaying various types of information, such as selected RF power level, frequency, and phase of each RF signal and the measured temperatures of the various body tissues. The front panel 104 may also include a keypad for entering user selectable information. The front panel 104 may also include an ON/OFF switch, RF ON/OFF switch, STAND-BY switch, POWER-UP/DOWN switch, and/or TIMER UP/DOWN switch.

Each control system 106, 108 generates control signals which control the operation of its respective waveform generator 110, 112 and power drive 114, 116. Each control system 106, 108 generates control signals in response to the initial commands from the microcontroller 102 and the feedback signals from the measurement systems 132, 134 and the temperature measurement system 136. Each waveform generator 110, 112 generates an RF signal having a specific frequency, phase and power level in accordance with the control and feedback signals. Each control system 106, 108 also includes an oscillator (not shown) for generating a clock signal that is used by its respective waveform generator for generating the RF signal.

Each waveform generator 110, 112 preferably generates an RF signal using a look-up table of various digital waveforms. The clock signal generated by the oscillator is used to retrieve the digital information and generate a digital RF waveform, which is converted to analog form using a digital-to-analog (D/A) converter. The various digitized waveforms can be stored in the RAM in microcontroller 102 and loaded into the look-up table as needed. The RF waveforms are preferably square or sinusoidal waveforms. The RF signals generated by the waveform generators 110, 112 are amplified by power drives 114 and 116. The gain of each power drive 114, 116 is controlled by its respective control system 106, 108.

The RF ablation device is used to ablate tissues inside the human body, so steps must be taken to isolate the patient from DC and very low frequency electrical signals which may cause harm to healthy tissues or organs. Isolators 118, 120 provide isolation of the patient from these potentially harmful signals. Each isolator is preferably a transformer having a primary and secondary winding and a ratio of the number of turns of the primary winding to the secondary winding of approximately Filters 122, 124 ensure that an RF signal with the desired frequency is applied to each electrode 26. Each filter 122, 124 includes a bank of bandpass filters which can be digitally selected by microcontroller 102. Command signals from the microcontroller 102 are sent on lines 140, 142 to the filters 122, 124, respectively.

RF ablation of human tissue raises the temperature of the tissue to a temperature at which the tissue is destroyed. It is very important to accurately control the amount of power that is delivered to the target tissue to accurately control this temperature, thus protecting the patient. Sensors 126, 128 provide this protection by measuring the RF current that is passed through the target tissue and the RF voltage applied across the tissue. These measurement signals are applied to their respective power measurement systems 132, 134 and to the differential sensor 130.

Power measurement systems 132, 134 generate feedback signals based on measurement signals provided by their respective sensors 126, 128 and the differential sensor 130. These feedback signals are used by microcontroller 102 and control systems 106 and 108 to control the operation of the RF power delivery system 100. Each power measurement system 132, 134 preferably includes an analog multiplier, means for measuring the root-mean-squared (RMS) value of each analog measurement signal, and an analog-to-digital (A/D) converter. The analog multiplier provides a measure of the RF power applied to each electrode 26 by multiplying the RF current and voltage measured by the sensors 126, 128. The RMS values of the measured current, voltage, and power are computed and then digitized by the A/D converter. These digitized measurement signals are then applied to the microcontroller 102 and the digitized power measurement is applied to the control systems 106, 108.

Temperature measurement system 136 generates digital feedback signals based on analog temperature measurement signals from the temperature sensors 42, 78, 80, 82. The digital temperature feedback signals are applied to microcontroller 102 and the control systems 106, 108.

The dual-channel RF power delivery system 100 has five different modes of operation, including SELF-TEST, STAND-BY, READY, RF ON, and RF OFF. When the power system is first turned on, the system enters the SELF-TEST mode. Various self-tests are performed in this mode, including a microprocessor test, RAM read/write test, a ROM test, an RF power generation and measurement test, and a temperature measurement system test. When the various tests are successfully passed, the system enters the STAND-BY mode. If the test is not passed, an error message appears on the display.

In the STAND-BY mode, power is supplied for the various functions, but none of the functions is active. When the READY switch on the front panel 104 is pressed, the system enters the READY mode.

In the READY mode, low-level RF signals are generated intermittently to allow impedance measurements to be made. The UP/DOWN POWER switch allows the desired power level for each electrode 26 to be incremented or decremented by 0.1 watt. The power range is limited to 0–15 watts. The UP/DOWN TIMER switch allows the desired time duration for each electrode 26 to be incremented or decremented by 1 second. The maximum time duration is typically limited to 10 minutes.

In the READY mode, temperature measurements are taken from each thermocouple. The two stylet temperatures are read ten times per second and a filtered average is displayed on the front panel 104, which is updated once per second. The urethral and rectal temperatures are also read ten times per second and a filtered average of the urethral temperature and a filtered maximum rectal temperature are displayed on the front panel 104. Impedance of the target tissue at the two electrodes 26 is measured by intermittently applying a low powered RF signal to each electrode and measuring the resulting RF voltage and RF current. The microcontroller 102 calculates the impedance by dividing the RF voltage by the RF current.

In the RF ON mode, RF power is generated and the measurement, control, display and timer functions are active. The RF ON mode is activated either by depressing the foot switch or the RF ON/OFF switch. Depressing the STANDBY switch or the foot switch reactivates the STANDBY mode. The RF OFF mode is automatically activated when the selected time durations for both stylets have been reached, or if any of the measured temperatures exceed predefined limits.

Figure 5:
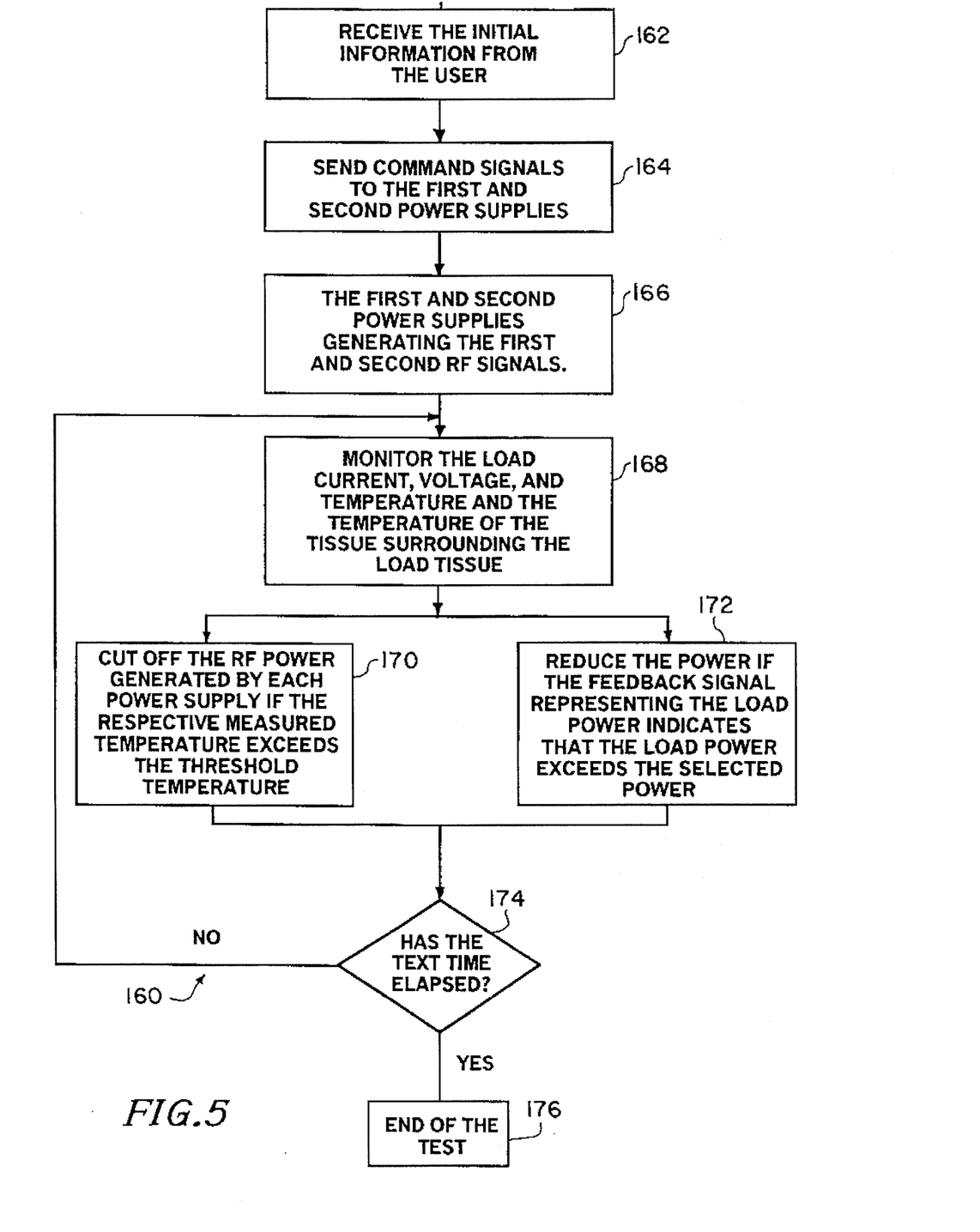
FIG. 5 is a flow chart of the sequence of operations of the RF power delivery system of the present invention.

FIG. 5 is a flow chart of the sequence of operations of the RF ON mode of the RF power delivery system 100 of the present invention. The user inputs the initial information in step 162. Initial information includes frequency, phase, power, and time duration for each RF signal. This information is typically entered using the keypad provided on the front panel 104. In step 164, the initial information is received by microcontroller 102, which generates digital command signals that are sent to control systems 106, 108 and filters 122, 124.

In step 166, the two power delivery channels generate two independent RF signals, with each RF signal having a selected power level, frequency, and phase. The RF power level is increased gradually toward the desired power level, at which time the RF signals are applied to their respective electrodes 26.

To protect the patient from receiving an excessive amount of RF energy, the RF power delivered to the target tissue is monitored by two different methods. The RF power levels are monitored either directly or through their effects on the target and surrounding tissues as indicated by the various temperature measurements. The RF power is monitored directly in step 168. Sensors 126, 128 measure the RF currents and RF voltages at the two electrodes 26. The power delivered to the target tissue is then calculated by the power measurement systems 132 and 134, as previously discussed.

Steps 170 and 172 may be performed simultaneously. In step 172, the power levels calculated by power measurement systems 132, 134 are compared with their respective selected power levels. The generated power levels are reduced if the measured power levels exceed their respective selected power levels. In step 170, RF power is terminated if the measured temperature of the target or the surrounding tissue exceeds a threshold temperature. RF power is delivered to the target tissue for a time duration as selected by the user. In step 174, after the selected time duration has expired, the power system enters the RF OFF mode.

The dual-channel RF power delivery system 100 of the present invention provides numerous advantages over prior art power delivery systems. The power delivery system 100 performs a battery of self-tests, including a test of each waveform generator 110, 112 by loading the generator with an internal test load. Precision reference voltage sources (not shown) are provided which can be used for calibrating the thermocouples. This test is implemented through a multiplexing scheme in which each thermocouple is individually calibrated using the reference voltages.

The use of multiplexers also allows temperature information to be easily obtained across the patient isolation barrier. An isolation barrier, such as a transformer-coupled or optically-coupled isolation amplifier, is usually required between a patient and a microcomputer. The use of the multiplexer arrangement avoids the need for separate isolation amplifiers for each thermocouple.

Figure 6:
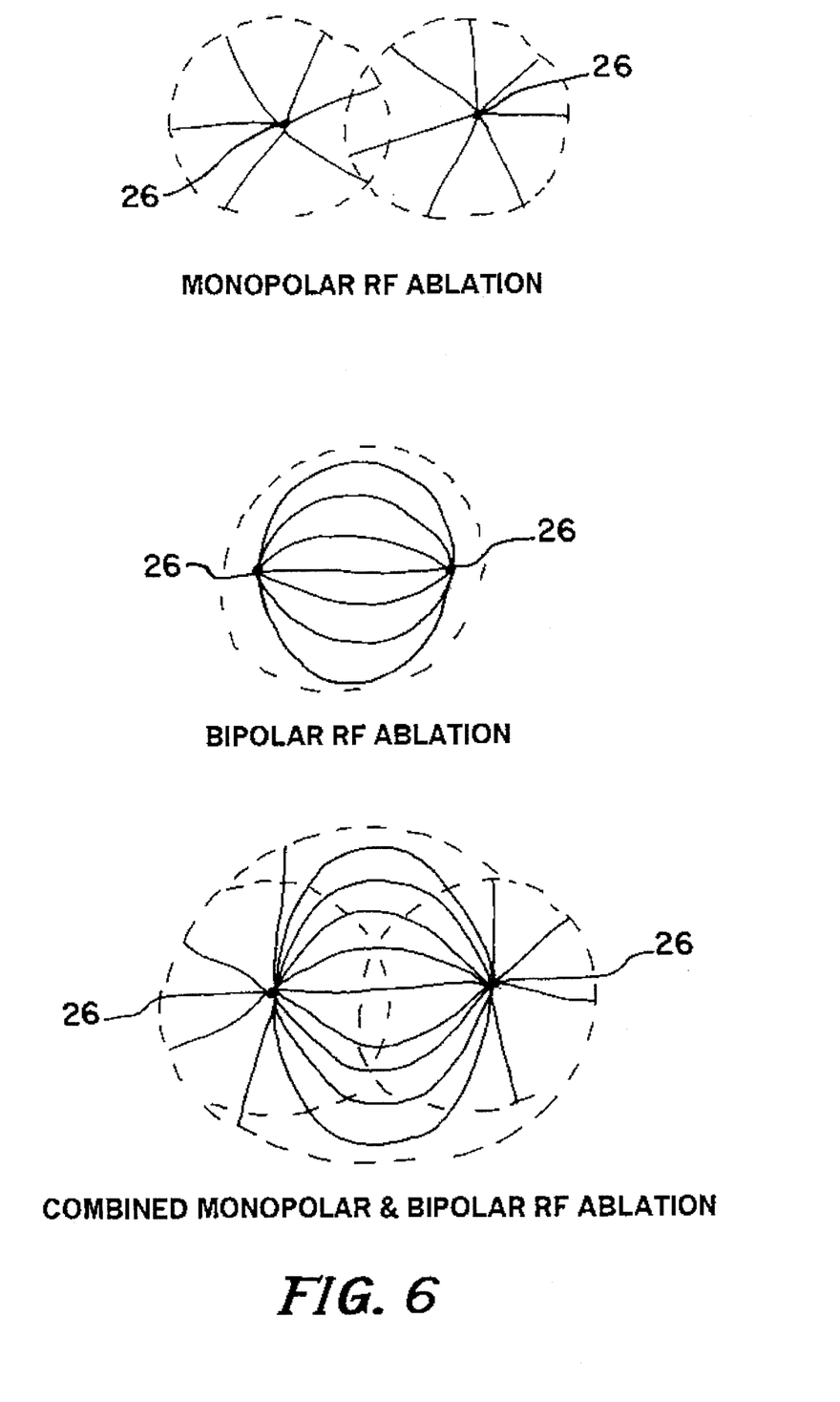
FIG. 6 is a schematic diagram of the effects of monopolar, bipolar, and combined monopolar and bipolar ablation on lesion volume.

Another significant advantage of the power delivery system 100 of the present invention is the availability of a combined monopolar and bipolar mode. In the monopolar mode, the same RF signal is applied to each electrode 26 and current flows from the electrodes to an indifferent electrode placed on the patient's back. The two RF signals are at the same power level, frequency, and phase. Therefore, the two electrodes 26 are at the same voltage levels and no current flows between them. Current only flows between each electrode and the indifferent electrode on the patient's back. However, by changing the power level, frequency or phase of one of the RF signals, a voltage is created across the electrodes 26 and current flows between them. This provides bipolar ablation in combination with monopolar ablation. Differential sensor 130 measures the difference in the current flows from the two electrodes 26 to the indifferent electrode. Bipolar ablation in combination with monopolar ablation allows a larger tissue volume to be ablated without increasing the RF energy applied to the patient. FIG. 6 is a schematic diagram of the lesion volumes provided by monopolar, bipolar, and combined monopolar and bipolar RF ablation.

The results of laboratory tests in which one of the RF signals was varied in phase, frequency, and phase and frequency are shown in Table 1. Turkey breasts were used as the target tissue.

TABLE 1

|  | TOTAL POWER (WATTS) | THE POWER OF THE FIRST ELECTRODE | THE POWER OF THE SECOND ELECTRODE | TIME (MIN.) | LESION VOLUME |
| --- | --- | --- | --- | --- | --- |
| 1. ONE SUPPLY | 8.2 | 4.1 | 4.1 | 5 | 1653 |
| 2. TWO POWER SUPPLIES AND PHASE DIFFERENCE | 4.1 (each supply) | 4.1 | 4.1 | 5 | 3600 |
| 3. TWO POWER SUPPLIES AND FREQUENCY DIFFERENCE | 4.1 (each supply) | 4.1 | 4.1 | 5 | 2135 |
| 4. TWO POWER SUPPLIES AND PHASE AND FREQUENCY DIFFERENCE | 4.1 (each supply) | 4.1 | 4.1 | 5 | 4582 |

In the first case, the same RF signal of 4.1 watts was applied to each electrode 26 for a total RF power level of 8.2 watts. In the second, third, and fourth cases, each RF signal had a power level of 4.1 watts, but the frequency, phase, and frequency and phase of one of the RF signals were varied. In the second case, the two RF signals were out of phase. In the third case, one RF signal had a frequency of 460 KHz and the other RF signal had a frequency of 480 KHz. In the fourth case, one RF signal had a frequency of 460 KHz the other RF signal had a frequency of 480 KHz and the RF signals were out of phase. In all four cases, the power was delivered to the target tissues for 5 minutes. In the fourth case, with the two RF signals out of phase and at different frequencies, the lesion volume was about three times the volume in the first case, which used identical RF signals.

From the foregoing, it will be appreciated that the present invention represents a significant advance in the field of RF ablation devices. Although several preferred embodiments of the invention have been shown and described, it will be apparent that other adaptations and modifications can be made without departing from the spirit and scope of invention. Accordingly, the invention is not to be limited, except as by the following claims.

What is claimed is:

1. Apparatus for the treatment by radio frequency ablation of a target volume of tissue of a prostate in a human male having a bladder with a base and a penis with a urethra therein formed by a urethral wall extending into the base of the bladder along a longitudinal axis with the tissue of the prostate surrounding the urethra near the base of the bladder comprising an indifferent electrode adapted to be placed in contact with the human male, an elongate probe member having proximal and distal extremities and being sized so that It can be introduced into the urethra and having a length so that when the distal extremity of the elongate probe member is disposed in the vicinity of the prostate, the proximal extremity extends out of the urethra, a control handle coupled to the proximal extremity of the elongate probe member, first and second stylers carried by the elongate probe member and being movable through the urethral wall into the target volume of tissue in the prostate, each of the stylers having an electrode and an insulating sleeve surrounding the electrode, radio frequency power supply means having first and second output channels of radio frequency energy, means coupling the first output channel to the electrode of the first styler and coupling the second output channel to the electrode of the second stylet, additional means coupling the indifferent electrode to the radio frequency power supply means, said radio frequency power supply means including control means for supplying radio frequency power simultaneously to the electrodes of the first and second stylets so that simultaneous ablation occurs in the target volume of the tissue in the prostate so that the lesion volume is approximately doubled over that which would be created by a single electrode for the same amount of time or conversely for the same lesion volume, the time required is reduced by approximately one-half.

2. Apparatus as in claim 1 wherein said radio frequency power supply means includes means for supplying radio frequency power to the first and second output channels so that the power level, frequency and phase are substantially the same whereby there is substantially no current flow between the electrodes of the first and second stylets.

3. Apparatus as in claim 1 wherein said radio frequency power supply means includes means for supplying radio frequency power from one of said first and second output channels to one of the electrodes of said first and second stylets and for causing the other of the electrodes of the first and second stylets to serve as a return electrode to cause bipolar ablation in the tissue of the prostate to form a lesion extending between the electrodes of the first and second stylets.

4. Apparatus as in claim 3 wherein said radio frequency power supply means includes means for supplying radio frequency energy from said one output channel at a different phase from the phase of the power being delivered to the electrodes of the first and second stylets so that radio frequency power can be delivered from the first and second output channels to the electrodes of the first and second stylets to perform monopolar ablation during the same time that bipolar ablation is being accomplished between the electrodes of the first and second stylets.

5. A method for the treatment by radio frequency ablation of a target volume of tissue of a prostate in a human male having a bladder with a base and a penis with a urethra therein formed by a urethral wall extending into the base of the bladder along a longitudinal axis with the tissue of the prostate surrounding the urethra near the base of the bladder by the use of an indifferent electrode in contact with the human male and an elongate probe member having proximal and distal extremities and sized so that it can be introduced into the urethra and having a length so that when the distal extremity of the elongate probe member is disposed in the vicinity of the prostate, the proximal extremity is proximal of the urethra, a control handle coupled to the proximal extremity of the elongate probe member, the elongate probe member having first and second stylets carried thereby and being movable through the urethral wall into the target volume of tissue in the prostate, each of the stylets having an electrode and an insulating sleeve surrounding the electrode and a radio frequency power supply having first and second output channels of radio frequency energy, means coupling the first output channel to the electrode of the first stylet and coupling the second output channel to the electrode of the second stylet comprising the steps of introducing the first and second stylets through the urethral wall and into the target volume of tissue in the prostate, supplying radio frequency energy from the first and second output channels simultaneously to the electrodes of the first and second stylets so that simultaneous ablation occurs at both of the electrodes to create a lesion volume which is approximately twice as great as that which can be created by a single electrode during the same period of time or conversely the same lesion volume can be created in approximately one-half of the time in comparison to the use of a single electrode.

6. A method as in claim 5 wherein the radio frequency power supplied by the first and second output channels is controlled to provide substantially the same power level, frequency and phase in both the first and second output channels for monopolar ablation.

7. A method as in claim 5 together with the step of supplying radio frequency power from said first output channel at a predetermined phase and utilizing the electrode of the other stylet as a return path for the radio frequency energy of the predetermined phase to provide bipolar ablation of the target volume of tissue.

8. A method as in claim 7 further comprising the steps of supplying radio frequency power from the first and second output channels to the electrodes of the first and second stylets at the same time that power is being supplied from said one output channel at a phase which is different from the phase of the power being supplied from the first and second output channels so that monopolar ablation of the tissue in the prostate is occurring at the same time that ablation is taking place in the target volume of tissue in the prostate by bipolar ablation.

* * * * *